(12) United States Patent
Boston

(10) Patent No.: US 9,707,006 B2
(45) Date of Patent: Jul. 18, 2017

(54) AORTIC ARCH RECONSTRUCTION DEVICE AND METHOD OF USING SAME

(71) Applicant: Umar S. Boston, St. Louis, MO (US)

(72) Inventor: Umar S. Boston, St. Louis, MO (US)

( * ) Notice: Subject to any disclaimer, the term of this patent is extended or adjusted under 35 U.S.C. 154(b) by 13 days.

(21) Appl. No.: 14/731,360

(22) Filed: Jun. 4, 2015

(65) Prior Publication Data

US 2015/0351786 A1    Dec. 10, 2015

Related U.S. Application Data

(60) Provisional application No. 62/007,492, filed on Jun. 4, 2014.

(51) Int. Cl.
| | | |
|---|---|---|
| *A61F 2/24* | (2006.01) | |
| *A61B 17/3205* | (2006.01) | |
| *A61B 17/32* | (2006.01) | |
| *A61B 17/00* | (2006.01) | |
| *A61B 90/00* | (2016.01) | |

(52) U.S. Cl.
CPC ......... *A61B 17/3205* (2013.01); *A61B 17/32* (2013.01); *A61B 2017/00778* (2013.01); *A61B 2017/320052* (2013.01); *A61B 2090/061* (2016.02); *A61B 2090/0807* (2016.02)

(58) Field of Classification Search
CPC ........................ A61F 2/2496; A61F 2002/762
USPC ......................... 600/587; 623/2.11
See application file for complete search history.

(56) References Cited

U.S. PATENT DOCUMENTS

| | | | |
|---|---|---|---|
| 8,721,676 B1 * | 5/2014 | Janardhan | A61B 17/12109 604/523 |
| 2013/0240491 A1 * | 9/2013 | Goodman, Jr. | B23K 10/00 219/121.44 |
| 2015/0133989 A1 * | 5/2015 | Lubock | A61B 17/0057 606/200 |
| 2015/0165110 A1 * | 6/2015 | Gopalakrishna | A61M 25/00 604/523 |
| 2016/0022157 A1 * | 1/2016 | Melker | A61B 5/021 600/407 |
| 2016/0213358 A1 * | 7/2016 | Amin | A61B 17/0057 |
| 2016/0243083 A1 * | 8/2016 | Anderson | A61K 9/0019 |

* cited by examiner

*Primary Examiner* — Suzette J Gherbi
(74) *Attorney, Agent, or Firm* — Bryan Cave LLP

(57) ABSTRACT

The present disclosure is directed to template devices and methods for using the same in aortic arch reconstruction.

20 Claims, 6 Drawing Sheets

Scale 2:1.

All dimensions are in millimeters.

Scale 2:1.

All dimensions are in millimeters.

AORTIC ARCH RECONSTRUCTION DEVICE AND METHOD OF USING SAME

FIELD OF THE INVENTION

The present invention generally relates to template devices for aortic arch reconstruction and methods of using the same.

BACKGROUND OF THE INVENTION

In some neonates, infants, and children, surgical repair of the aortic arch is necessary to correct certain defects caused, for example, by hypoplastic left heart syndrome, interrupted aortic arch, hypoplastic aortic arch and complex aortic coarctation.

The congenital heart defect known as hypoplastic left heart syndrome, for example, leads to hypoplastic development of the aortic arch (that is, aortic arch hypoplasia). Neonates having this syndrome are palliated with an operation known as the Norwood procedure in which arch reconstruction is an essential component. (1,2). Among the limitations of arch reconstruction is that if the patch is not shaped appropriately, then there can be stenosis (narrowing) in the aortic arch which can lead to obstruction of the flow of blood to the body. (3-5). Furthermore, this narrowing can place a tremendous strain on the right ventricle which can lead to significant dysfunction and eventually heart failure and shock if left untreated. Treatment of recurrent narrowing of the reconstructed arch requires either a catheter based balloon dilatation or another open heart operation to repair the narrowed sight (6-12).

SUMMARY OF THE INVENTION

Among the various aspects of the present invention is the provision of template devices for aortic arch reconstruction and methods of using the same.

Briefly, therefore, the present invention is directed to a template device for use in aortic arch reconstruction, having the shape and dimensions as the template depicted in FIGS. 1A and 1B.

Another aspect of the invention is directed to a template device for use in aortic arch reconstruction, having the shape and dimensions as the template depicted in FIG. 1C.

Yet another aspect of the invention is directed to a method for the reconstruction of hypoplasia of the aortic arc, the method comprising shaping a patch using a template device described herein.

Other objects and features will be in part apparent and in part pointed out hereinafter.

BRIEF DESCRIPTION OF THE DRAWINGS

The above mentioned and other features of the present invention and the manner of obtaining them will become more apparent and the invention will be best understood by reference to the following description of embodiments of the invention taken in conjunction with the accompanying drawings, in which like numerals refer to like parts, and in which.

DETAILED DESCRIPTION

The accompanying Figures and this description depict and describe embodiments of a template and method for using same in accordance with the present invention, and features and components thereof. It should also be noted that any references herein to front and back, right and left, top and bottom and upper and lower are intended for convenience of description, not to limit the present invention or its components to any one positional or spatial orientation.

Template Device

One aspect of the present invention is directed to a template device having a geometry as shown and described.

Figure 1A:
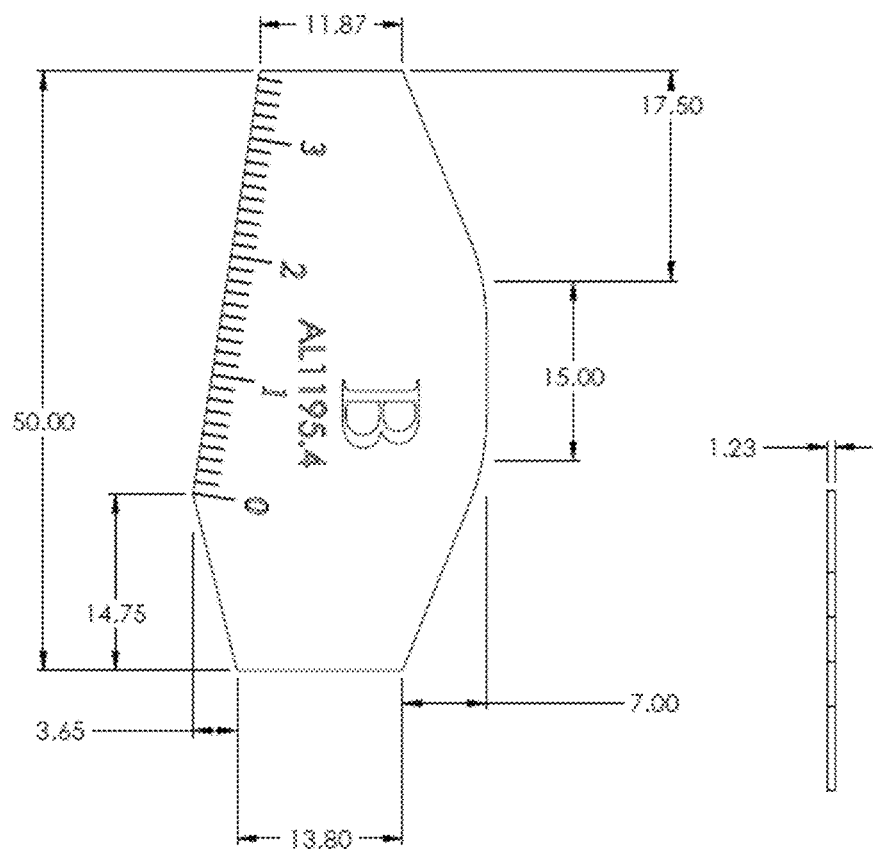
FIGS. 1A, 1B, and 1C depict template devices in accordance with embodiments of the present disclosure.
Figure 1B:
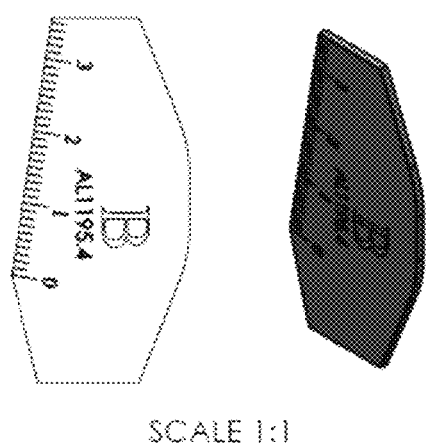

In accordance with one embodiment, the template device has the shape and dimensions as depicted in FIGS. 1A and 1B. In one particular embodiment, the generally heptagonal-shaped template device has the following dimensions: 15 mm (proximal end)×[20 mm×15 mm×15 mm (greater curvature)]×[35 mm×15 mm (lesser curvature)]×10 mm (distal end).

Figure 1C:
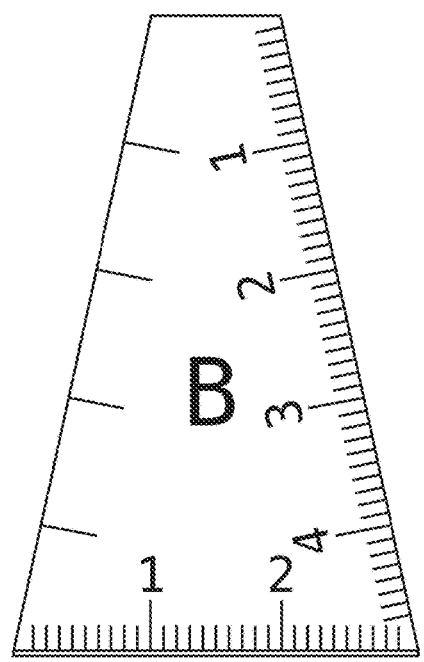

In accordance with another embodiment, the template device has the shape and dimensions as depicted in FIG. 1C. In one particular embodiment, the generally quadrilateral-shaped template device has the following dimensions: 30 mm (proximal end)×50 mm (greater curvature)×50 mm (lesser curvature)×10 mm (distal end).

In either of the preceding embodiments (i.e., FIGS. 1A/1B or 1C), the aforementioned dimensions of the template device may be increased, for instance, so that the device may be used in infants or older children. For example, in some embodiments, the aforementioned dimensions for the template device of FIGS. 1A/1B may be at least 1% greater, at least 2.5% greater, at least 5% greater, at least 10% greater, at least 15% greater, at least 20% greater, at least 25% greater, at least 30% greater, at least 35% greater, at least 40% greater, at least 45% greater, or at least 50% greater, in one or more directions. Similarly, for example, in some embodiments, the aforementioned dimensions for the template device of FIG. 1C may be at least 1% greater, at least 2.5% greater, at least 5% greater, at least 10% greater, at least 15% greater, at least 20% greater, at least 25% greater, at least 30% greater, at least 35% greater, at least 40% greater, at least 45% greater, or at least 50% greater, in one or more directions.

The template device is construction from any durable material capable of withstanding high temperatures during sterilization of the device prior to use. In this regard, plastics may be less preferred, while metals are more preferred. In one preferred embodiment, the template device is constructed from is stainless steel. In general, the template device is intended to be re-used multiple times for multiple procedures. It will be understood, however, that disposable embodiments of the template device are contemplated.

As depicted in FIGS. 1A, 1B, and 1C, the template device may in some embodiments include ruler markings and numbers. Other indicia may also optionally be provided.

Methods of Using the Template Device

In accordance with one aspect of the present disclosure, the device described herein may be employed in a method for shaping patches for the reconstruction of hypoplasia of the aortic arch, particularly (but not necessarily exclusively) for neonates and infants.

Figure 2:
FIGS. 2-7 are photographs of steps performed in connection with a method for shaping patches for the reconstruction of hypoplasia of the aortic arch using an embodiment of the template device described herein.
Figure 3:
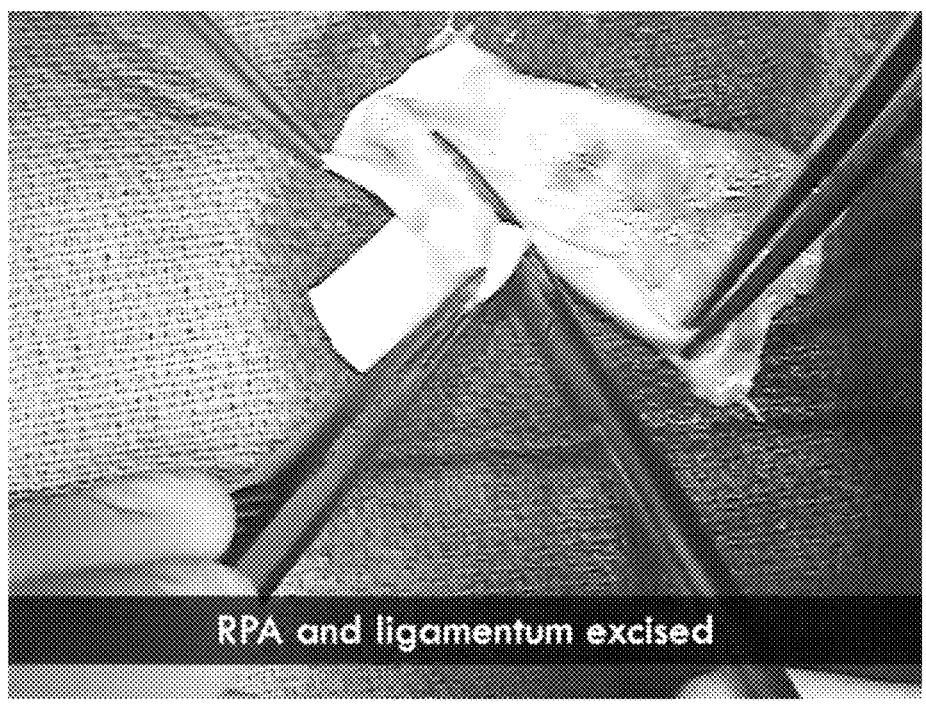
Figure 4:
Figure 5:
Figure 6:
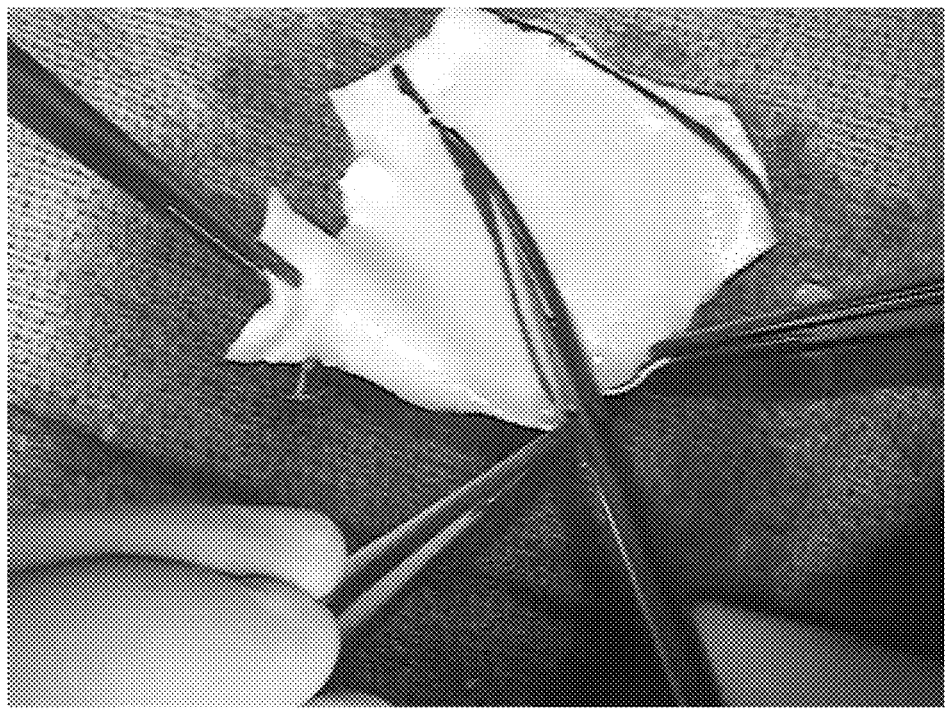
Figure 7:
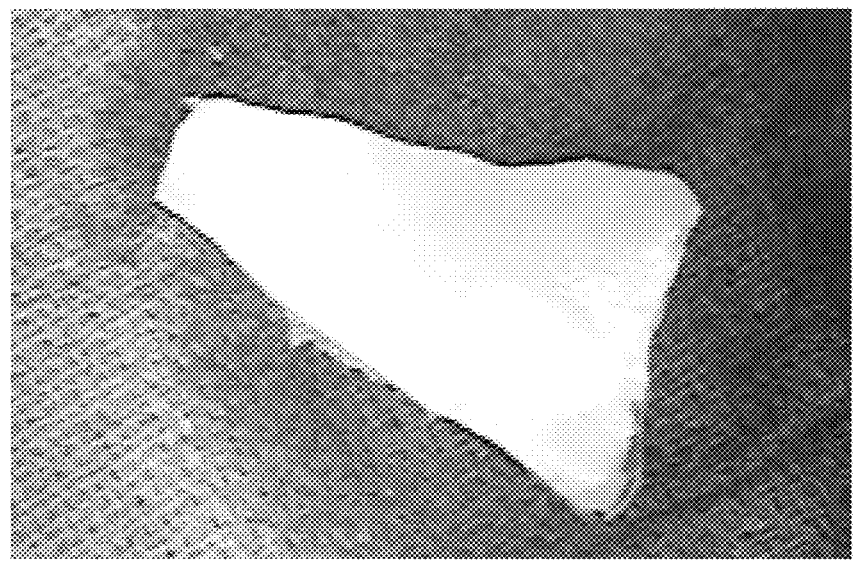

The method generally involves using the template device to shape the patch that will be used to reconstruct the aortic arch. Typically, pulmonary homograft tissue is used for the patch. First, the patch is thawed and the attached muscular tissue and leaflets are transected. See FIGS. 2 and 3. The pulmonary homograft tissue is then "filleted" opened, by incising along the right lateral wall of the main pulmonary artery and transecting the right branch pulmonary artery. An incision from the orifice of the right pulmonary artery proximally opens up the patch. See FIG. 4. The template device is used to mark the patch of pulmonary homograft (e.g., using a sterile pen). See FIG. 5. The patch of pulmonary homograft tissue is then cut along the boundaries outlined by the template. See FIGS. 6 and 7. This tailored patch is now ready for use to reconstruct the aortic arch in accordance with conventional techniques.

In accordance with another aspect of the present disclosure, the device described herein may be employed as a measuring tool in a method for performing congenital heart surgery. By way of example, in congenital heart surgery there is a need for measuring a variety of patches used, for instance, to repair defects such as atrial and ventricular septal defects, or to measure patches to reconstruct other vessels than the aortic arch, e.g., pulmonary arteries.

REFERENCES

1. Norwood, W I; Lang, P; Casteneda, A R; Campbell, D N. Experience with operations for hypoplastic left heart syndrome. J Thorac and Cardiovasc Surg. 1981; 82 (4): 511-9

2. Norwood, William I.; Lang, Peter; Hansen, Dolly D. (6 Jan. 1983). "Physiologic Repair of Aortic Atresia-Hypoplastic Left Heart Syndrome". New England Journal of Medicine 308 (1): 23-26

3. Ashcraft T M, Jones K, Border W L, Eghtesady P, Pearl J, Khoury P R, Manning P B. Factors affecting long-term risk of aortic arch recoarctation after the Norwood procedure. *Ann Thorac Surq* 2008 April; 85(4):1397-401.

4. Zeltser I, Menteer J, Gaynor W, Spray T L, Clark B J, Kreutzer J, Rome J J. Impact of re-coarctation following the Norwood operation on survival in the balloon angioplasty era. *J Am Coll Cardiol.* 2005; 45(11):1844-1848.

5. Cleuziou J, Kasnar-Samprec J, Hörer J, Eicken A, Lange R, Schreiber C. Recoarctation after the Norwood I Procedure for Hypoplastic Left Heart Syndrome: Incidence, Risk Factors, and Treatment Options. Ann Thorac Surg 2013; 95:935-940

6. Hornik C P, He X, Jacobs J P, et al. Complications after the Norwood Operation: an analysis of the Society of Thoracic Surgeons Congenital Heart Surgery database. Ann Thorac Surg 2011; 92:1734-41.

7. Burkhart H M, Ashburn D A, Konstantinov I E, et al. Interdigitating arch reconstruction eliminates recurrent coarctation after the Norwood procedure. J Thorac Cardiovasc Surg 2005; 130:61-5.

8. Ishino K, Stümper O, De Giovanni J J, et al. The modified Norwood procedure for hypoplastic left heart syndrome: early to intermediate results of 120 patients with particular reference to aortic arch repair. J Thorac Card iovasc Surg 1999; 117:1920-30.

9. Lamers L J, Frommelt P C, Mussatto K A, Jaquiss R D B, Mitchell M E, Tweddell J S. Coarctectomy combined with an interdigitating arch reconstruction results in a lower incidence of recurrent arch obstruction after the Norwood procedure than coarctectomy alone. J Thorac Cardiovasc Surg 2012; 143:1098-102.

10. Larrazabal L A, Selamet Tierney E S, Brown D W, et al. Ventricular function deteriorates with recurrent coarctation in hypoplastic left heart syndrome. Ann Thorac Surg 2008;86: 869-74.

11. Porras D, Brown D W, Marshall A C, Del Nido P, Bacha E A, McElhinney DB. Factors associated with subsequent arch reintervention after initial balloon aortoplasty in patients with Norwood procedure and arch obstruction. J Am Coll Cardiol 2011; 58:868-76.

12. Mahle W. T., Spray T. L., Wernovsky G., Gaynor J. W., Clark B. J. Survival after reconstructive surgery for hypoplastic left heart syndrome: a 15-year experience from a single institution. Circulation 2000; 102 (Suppl. 3):111136-141.

Having described the invention in detail, it will be apparent that modifications and variations are possible without departing the scope of the invention defined in the appended claims. Furthermore, it should be appreciated that all examples in the present disclosure are provided as non-limiting examples.

What is claimed is:

1. A template device comprising:
a generally heptagonal-shaped template for use in aortic arch reconstruction comprising:
 a proximal end having a length in a range of about 15 mm to about 22.5 mm;
 a distal end having a length in a range of about 10 mm to about 15 mm;
 a greater curvature extending between the proximal end and the distal end, the greater curvature comprising a first segment extending from the proximal end and having a length in a range of about 20 mm to about 30 mm, a second segment extending from the distal end and having a length in a range of about 15 mm to about 22.5 mm, and a third segment extending between the first and second segments and having a length in a range of about 15 mm to about 22.5 mm; and
 a lesser curvature extending between the proximal end and the distal end opposite the greater curvature, the lesser curvature comprising a first segment extending from the proximal end and having a length in a range of about 15 mm to about 22.5 mm, and a second segment extending from the first segment to the distal end and having a length in a range of about 35 mm to about 52.5 mm.

2. A template device comprising:
a generally quadrilateral-shaped template for use in aortic arch reconstruction comprising:
 a proximal end having a length in a range of about 30 mm to about 45 mm;
 a distal end having a length in a range of about 10 mm to about 15 mm;
 a greater curvature extending between the proximal end and the distal end and having a length in a range of about 50 mm to about 75 mm; and
 a lesser curvature extending between the proximal end and the distal end opposite the greater curvature and having a length in a range of about 50 mm to about 75 mm.

3. The template device of claim 1, wherein the template device comprises stainless steel.

4. The template device of claim 1, wherein the template device includes ruler markings and numbers.

5. A method for the reconstruction of hypoplasia of the aortic arc, the method comprising shaping a patch using the template device of claim 1.

6. The template device of claim 2, wherein the template device comprises stainless steel.

7. The template device of claim 2, wherein the template device includes ruler markings and numbers.

8. A method for the reconstruction of hypoplasia of the aortic arc, the method comprising shaping a patch using the template device of claim 2.

9. The template device of claim 2, wherein the generally quadrilateral-shaped template is generally planar.

10. The template device of claim 2, wherein the proximal end has a length of about 30 mm.

11. The template device of claim 2, wherein the distal end has a length of about 10 mm.

12. The template device of claim 2, wherein the greater curvature has a length of about 50 mm.

13. The template device of claim 2, wherein the lesser curvature has a length of about 50 mm.

14. The template device of claim 2, wherein the proximal end has a length of about 30 mm, the distal end has a length of about 10 mm, the greater curvature has a length of about 50 mm, and the lesser curvature has a length of about 50 mm.

15. The template device of claim 1, wherein the generally heptagonal-shaped template is generally planar.

16. The template device of claim 1, wherein the proximal end has a length of about 15 mm.

17. The template device of claim 1, wherein the distal end has a length of about 10 mm.

18. The template device of claim 1, wherein the first segment of the greater curvature has a length of about 20 mm, the second segment of the greater curvature has a length of about 15 mm, and the third segment of the greater curvature has a length of about 15 mm.

19. The template device of claim 2, wherein the first segment of the lesser curvature has a length of about 15 mm and the second segment of the lesser curvature has a length of about 35 mm.

20. The template device of claim 2, wherein the proximal end has a length of about 15 mm, the distal end has a length of about 10 mm, the first segment of the greater curvature has a length of about 20 mm, the second segment of the greater curvature has a length of about 15 mm, the third segment of the greater curvature has a length of about 15 mm, the first segment of the lesser curvature has a length of about 15 mm, and the second segment of the lesser curvature has a length of about 35 mm.

* * * * *